US008003781B2

(12) United States Patent
Kondo et al.

(10) Patent No.: US 8,003,781 B2
(45) Date of Patent: Aug. 23, 2011

(54) COMPOSITION FOR SUPPRESSING THE EXPRESSION OF FUCOSYLTRANSFERASE (75) Inventors: Akihiro Kondo, Suita (JP); Wenzhe Li, Suita (JP); Takatoshi Nakagawa, Suita (JP); Nobuto Koyama, Otsu (JP); Naoyuki Taniguchi, Osaka (JP); Ikunoshin Kato, Otsu (JP)

(73) Assignees: Osaka University, Osaka (JP); Takara Bio Inc., Shiga (JP)

( * ) Notice: Subject to any disclaimer, the term of this patent is extended or adjusted under 35 U.S.C. 154(b) by 0 days.

(21) Appl. No.: 12/281,601

(22) PCT Filed: Mar. 2, 2007

(86) PCT No.: PCT/JP2007/054035
§ 371 (c)(1),
(2), (4) Date: Jan. 6, 2009

(87) PCT Pub. No.: WO2007/100091
PCT Pub. Date: Sep. 7, 2007

(65) Prior Publication Data
US 2009/0221065 A1 Sep. 3, 2009

(30) Foreign Application Priority Data
Mar. 3, 2006 (JP) .................. 2006-057036

(51) Int. Cl.
*C07H 21/02* (2006.01)
*C07H 21/04* (2006.01)
(52) U.S. Cl. ............... 536/24.5; 536/23.1; 536/24.3; 536/24.33

(58) Field of Classification Search ................. 536/23.1, 536/24.3, 24.33, 24.5
See application file for complete search history.

(56) References Cited

U.S. PATENT DOCUMENTS
2004/0132140 A1 7/2004 Satoh et al.
2006/0223147 A1 10/2006 Nishiya et al.
2007/0134759 A1 6/2007 Nishiya et al.

FOREIGN PATENT DOCUMENTS
JP 2005/058111 A 3/2005
JP 2005224240 A 8/2005

OTHER PUBLICATIONS
Ryther et al. siRNA therapeutics: big potential from small RNAs. Gene Therapy, 2005 vol. 12, pp. 5-11.*
Ito et al. (Cancer Letters, 2003, vol. 200:167-172).*
K. Noda, et al., "Relationship between elevated FX expression and increased production of GDP-L-Fucose, a common donor substrate for fucosylation in human hepatocellular carcinoma and hepatoma cell lines", Cancer Rersearch, Oct. 1, 2003, p. 6282-6289, vol. 63.
S. Yanagidani, et al., "Purification and cDNA cloning of GDP-L-Fuc: N-Acetyl-β-D-Glucosaminide: α1-6 Fucosyltransferase (α1-6 FucT) from human gastric cancer MKN45 cells", J. Biochem, 1997, p. 626-632, vol. 121, No. 3.

(Continued)

*Primary Examiner* — Sean McGarry
*Assistant Examiner* — Terra Cotta Gibbs
(74) *Attorney, Agent, or Firm* — Browdy and Neimark, PLLC (57) ABSTRACT Disclosed is a means for reducing the expression amount of a FUT8 gene, reducing the expression amount of a FUT8 protein, and/or reducing the expression amount of a product produced by the action of FUT8.

15 Claims, 2 Drawing Sheets

OTHER PUBLICATIONS

H. Hayashi, et al., "Molecular cloning of mouse Alpha-1, 6-Fucosyltransferase and expression of its mRNA in the developing cerebrum", DNA Sequence, 2000, p. 91-96, vol. 11(1-2), Overseas Publishers Association.

N. Caplen, et al., "Specific inhibition of gene expression by small double-stranded RNAs in invertebrate and vertebrate systems", Proc. Natl. Acid. Sci., Aug. 14, 2001, p. 9742-9747, vol. 98, No. 17.

"Letters to nature", Nature, May 24, 2001, p. 494-498, vol. 411, Macmillan Magazines Ltd.

A. Kondo, et al., "A basic investigation on suppression of the proliferation of hepatic cancer cells through suppression of glycosylrtransferase", Acta Hepatologica Japonica, 2005, p. A144(O-138), vol. No. 46 suppl. 1.

N. Taniguchi, et al., "Functional glycomics and evidence for gain- and loss-of-functions of target proteins for glycosyltransferasees involved in N-glycan biosynthesis: their pivotal roles in growth and development, cancer metastasis and antibody therapy against cancer", Poc. Japan Acad., Ser. B, 2004, p. 82-91, vol. 80.

K. Mori, et al., "Engineering chinese hamster ovary cells to maximze effector function of produced antibodies using FUT8 siRNA", Biotechnology and Bioengineering, Dec. 30, 2004, p. 901-908, vol. 88, No. 7, Wiley Periodicals.

* cited by examiner

SEQUENCE LISTING

```
<160> NUMBER OF SEQ ID NOS: 21

<210> SEQ ID NO 1
<211> LENGTH: 19
<212> TYPE: RNA
<213> ORGANISM: Artificial Sequence
<220> FEATURE:
<223> OTHER INFORMATION: RNA which represses the function of FUT8 mRNA

<400> SEQUENCE: 1
caggcuuaua ucccuccua                                                      19

<210> SEQ ID NO 2
<211> LENGTH: 19
<212> TYPE: RNA
<213> ORGANISM: Artificial Sequence
<220> FEATURE:
<223> OTHER INFORMATION: RNA which represses the function of FUT8 mRNA
```

-continued

<400> SEQUENCE: 2
uggagcuaaa gagcucugg                                              19

<210> SEQ ID NO 3
<211> LENGTH: 19
<212> TYPE: RNA
<213> ORGANISM: Artificial Sequence
<220> FEATURE:
<223> OTHER INFORMATION: RNA which represses the function of FUT8 mRNA

<400> SEQUENCE: 3
ucucagaauu ggcgcuaug                                              19

<210> SEQ ID NO 4
<211> LENGTH: 19
<212> TYPE: RNA
<213> ORGANISM: Artificial Sequence
<220> FEATURE:
<223> OTHER INFORMATION: RNA which represses the function of FUT8 mRNA

<400> SEQUENCE: 4
cagcuuguua aggccaaag                                              19

<210> SEQ ID NO 5
<211> LENGTH: 13
<212> TYPE: RNA
<213> ORGANISM: Artificial Sequence
<220> FEATURE:
<223> OTHER INFORMATION: RNA which represses the function of FUT8 mRNA

<400> SEQUENCE: 5
uauaucccuc cua                                                    13

<210> SEQ ID NO 6
<211> LENGTH: 13
<212> TYPE: RNA
<213> ORGANISM: Artificial Sequence
<220> FEATURE:
<223> OTHER INFORMATION: RNA which represses the function of FUT8 mRNA

<400> SEQUENCE: 6
agcuaaagag cuc                                                    13

<210> SEQ ID NO 7
<211> LENGTH: 13
<212> TYPE: RNA
<213> ORGANISM: Artificial Sequence
<220> FEATURE:
<223> OTHER INFORMATION: RNA which represses the function of FUT8 mRNA

<400> SEQUENCE: 7
cagaauuggc gcu                                                    13

<210> SEQ ID NO 8
<211> LENGTH: 13
<212> TYPE: RNA
<213> ORGANISM: Artificial Sequence
<220> FEATURE:
<223> OTHER INFORMATION: RNA which represses the function of FUT8 mRNA

<400> SEQUENCE: 8
guuaaggcca aag                                                    13

<210> SEQ ID NO 9
<211> LENGTH: 3775

<212> TYPE: RNA
<213> ORGANISM: Homo sapiens

<400> SEQUENCE: 9

```
cguuuaguac agaaaucuca ugggagagag cauccaugca uuuacaaauu guuauugaau      60
uauuuuauug aaugaugaca cccaaacuga gcuagaacau aauucuggcu cugcuaguac     120
aucuucugug ugaucuugga caagucacuc uacuuuccuu ucaauuuucu uuucucacag     180
ggagauaauc auaaaaacga cuguaaagua cagcacuuca uagagugcuu uuuguuuaaa     240
gagcugacaa uaaauacgag ucucaagguc uaggaaagcc ucccucacaa ccugagcugc     300
uugaggacaa gggauuuucu uuugaaucag caguaccuua uuuguguauc ugugauagag     360
uuccugguac auaagaaggu cucaauaaau augugaauuu augaauauua ggcagauugc     420
aaccuugaca ggccacugcc ucuuaaaucu ccuuucugug aucuuuuaau auuuaacauc     480
uaaaaggccg ccgcuacuug cuuugggaua aguaucccg guauguacuu uaaaaugccc      540
aagccuagag aaaugauucu ugucuaagg gcaccauuuc gcucucccac cguaaagcgc      600
cccaggcuug ggaucugggu cccaaggcua caggggaagag uuggaacgg gaagcucauc      660
uuccggcccu cugauuggcc ggcucgcacu ccacucacgg ggcgcgcagc ucugauuggc      720
cucggcggca ccccucgucc cgcgacuacu uugugugcug gggcggcgcg cuccgguccu     780
cccgcucagc uggcggucug ggcugcucug ggcagcccu ucgguccacu gcucugcauc      840
gcgggcgccg ggaauuuucc gagugccgagc ggguugcugc uuuugcucag aggacaucca     900
ugacccuaau ggucuuuuug uucaagauaa agugauuuuu ugccuuuguu gauuaacugg     960
acaaauucag caugagagc gcaugaagua caggacaaua aagcuuccua cacauaucac    1020
caggaggauc ucuuugaaag auucacugca ggacuaccag agagaauaau uugcugaag     1080
caucaugugu ugaaacaaca gaagucuauu caccugugca cuaacuagaa acagaguuac    1140
aauguuuuca auucuuugag cuccaggacu ccagggaagu gaguugaaaa ucugaaaaug    1200
cggccaugga cugguuccug gcguuggauu augcucauuc uuuuugccug ggggaccuug    1260
cuguuuuaua uaggugguca cuggguacga gauaaugacc auccgaauca cucuagccga    1320
gaacugucca agauucuggc aaagcuugaa cgcuuaaaac aacagaauga agacuugagg    1380
cgaauggccg aaucucuccg gauaccagaa ggcccuauug ucaggggcc agcuauagga     1440
agaguacgcg uuuuagaaga gcagcuuguu aaggccaaag aacagauuga aaauuacaag    1500
aaacagacca gaaauggucu ggggaaggau caugaaaucc ugaggaggag gauugaaaau    1560
ggagcuaaag agcucuggu uuuuccuaac agugaauuga gaaauuaaaa gaacuuagaa     1620
ggaaaugaac uccaaagaca ucagaugaa uuucuuuugg auuaggaca ucaugaaagg      1680
ucuauaauga cggaucuaua cuaccucagu cagacagaug gagcagguga uuggcgggaa    1740
aaagaggcca aagaucugac agaacugguu cagcgggagaa uaacauaucu ucagaauccc    1800
aaggacugca gcaaagccaa aaagcugguu guaauauca acaaaggcug uggcuauggc    1860
ugucagcucc aucauguggu cuacugcuuc augauugcau auggcacccca gcgaacacuc    1920
aucuuggaau ucagaauug gcgcuaugcu acgguggau gggagacugu auuuaggccu    1980
guaagugaga caugcacaga cagaucuggc aucuccacug acacgguc agguggauguu     2040
aaggacaaaa auguucaagu ggcgagcuu cccauguag acagucuuca uccccgucu      2100
ccauauuuac ccuuggcugu accagaagac cucgcagauc gacuugugcg agugcaugu    2160
gacccugcag ugugggguggu gucucaguuu gucaauacug gauccgccc acagccuggg    2220
cuagaaaaag aaauagaaga gccaccaag aagcuuggcu ucaaacaucc aguuauugga    2280
```

```
guccauguca gacgcacaga caaaguggga acagaagcug ccuuccaucc cauugaagag    2340 uacaugguge auguugaaga acauuuucag cuucuugcac gcagaaugca aguggacaaa    2400
aaaagagugu auuuggccac agaugacccu ucuuuauuaa aggaggcaaa acaaaguac     2460 cccaauuaug aauuuauuag ugauaacucu auuccuggu cagcuggacu gcacaaucga    2520
uacacagaaa auucacuucg uggagugauc cuggauauac auuuucucuc ucaggcagac    2580
uuccuagugu guacuuuuuc aucccagguc ugucgaguug cuuaugaaau uaugcaaaca    2640
cuacauccug augccucugc aaacuuccau ucuuuagaug acaucuacua uuuuggggc     2700 cagaaugccc acaaucaaau ugccauuuau gcucaccaac cccgaacugc agaugaaauu    2760
cccauggaac cuggagauau cauuggugug gcuggaaauc auugggaugg cuauucuaaa    2820
ggugucaaca ggaaauuggg aaggacgggc cuauaucccu ccuacaaagu cgagagaag     2880 auagaaacgg ucaaguaccc cacauauccu gaggcugaga auaaagcuc agauggaaga    2940 gauaaacgac caaacucagu ucgaccaaac ucaguucaaa ccauucagc caaacuguag    3000 augaagaggg cucugaucua acaaaauaag guuauaugag uagauacucu cagcaccaag    3060
agcagcuggg aacugacaua ggcuucaauu gguggaauuc cucuuuaaca agggcugcaa    3120
ugcccucaua cccaugcaca guacaauaau guacucacau auaacaugca aacagguugu    3180
uuucuacuuu gccccuuuca guaugccccc auaagacaaa cacugccaua uuguguaauu    3240
uaagugacac agacauuuug ugugagacuu aaaacauggu gccuauaucu gagagaccug    3300
ugugaacuau ugaagagauc ggaacagcuc cuuacucuga ggaaguugau ucuuauuuga    3360
uggugguauu gugaccacug aauucacucc agucaacaga uucagaauga gaauggacgu    3420
uugguuuuuu uuguuuuug uuuuuguuuu uccuuuauu agguugucug uuuuuuuuu      3480 uuuaaauaau ugcaucaguu cauugaccuc aucauuaaua agugaagaau acaucagaaa    3540
auaaaauauu cacucuccau uagaaaauuu uguaaaacaa ugccaugaac aaauucuuua    3600
guacucaaug uuucuggaca uucucuuuga uaacaaaaaa uaaauuuuaa aaaggaauuu    3660
uguaaaguuu cuagaauuuu auaucauugg augauauguu gaucagccuu auguggaaga    3720
acugugauaa aaagaggage uuuuuaguuu uucagcuuaa aaaaaaaaaa aaaaa         3775
```

```
<210> SEQ ID NO 10
<211> LENGTH: 21
<212> TYPE: DNA
<213> ORGANISM: Artificial Sequence
<220> FEATURE:
<223> OTHER INFORMATION: Primer to amplify a DNA fragment derived from
      mouse FUT8 mRNA

<400> SEQUENCE: 10
aacagcttgt taaggccaaa g                                              21

<210> SEQ ID NO 11
<211> LENGTH: 22
<212> TYPE: DNA
<213> ORGANISM: Artificial Sequence
<220> FEATURE:
<223> OTHER INFORMATION: Primer to amplify a DNA fragment derived from
      mouse FUT8 mRNA

<400> SEQUENCE: 11
gcatgtcttt ggagttcatt tc                                             22

<210> SEQ ID NO 12
<211> LENGTH: 20
```

```
<212> TYPE: DNA
<213> ORGANISM: Artificial Sequence
<220> FEATURE:
<223> OTHER INFORMATION: Primer to amplify a DNA fragment derived from
      mouse GAPDH mRNA

<400> SEQUENCE: 12
aaatggtgaa ggtcggtgtg                                                     20

<210> SEQ ID NO 13
<211> LENGTH: 18
<212> TYPE: DNA
<213> ORGANISM: Artificial Sequence
<220> FEATURE:
<223> OTHER INFORMATION: Primer to amplify a DNA fragment derived from
      mouse GAPDH mRNA

<400> SEQUENCE: 13 tgaagggtc gttgatgg                                                        18

<210> SEQ ID NO 14
<211> LENGTH: 62
<212> TYPE: DNA
<213> ORGANISM: Artificial Sequence
<220> FEATURE:
<223> OTHER INFORMATION: DNA encoding stem-loop RNA which represses the
      function of FUT8 mRNA

<400> SEQUENCE: 14
gatccgtctc agaattggcg ctatgttcaa gagacatagc gccaattctg agactttttt         60
at                                                                        62

<210> SEQ ID NO 15
<211> LENGTH: 60
<212> TYPE: DNA
<213> ORGANISM: Artificial Sequence
<220> FEATURE:
<223> OTHER INFORMATION: DNA encoding stem-loop RNA which represses the
      function of FUT8 mRNA

<400> SEQUENCE: 15
cgataaaaaa gtctcagaat tggcgctatg tctcttgaac atagcgccaa ttctgagacg         60

<210> SEQ ID NO 16
<211> LENGTH: 62
<212> TYPE: DNA
<213> ORGANISM: Artificial Sequence
<220> FEATURE:
<223> OTHER INFORMATION: DNA encoding stem-loop RNA which represses the
      function of FUT8 mRNA

<400> SEQUENCE: 16
gatccgcagc uuguuaaggc caaagttcaa gagactttgg ccttaacaag ctgctttttt         60
at                                                                        62

<210> SEQ ID NO 17
<211> LENGTH: 60
<212> TYPE: DNA
<213> ORGANISM: Artificial Sequence
<220> FEATURE:
<223> OTHER INFORMATION: DNA encoding stem-loop RNA which represses the
      function of FUT8 mRNA

<400> SEQUENCE: 17
cgataaaaaa gcagcuuguu aaggccaaag tctcttgaac tttggcctta acaagctgcg         60
```

```
<210> SEQ ID NO 18
<211> LENGTH: 21
<212> TYPE: DNA
<213> ORGANISM: Artificial Sequence
<220> FEATURE:
<223> OTHER INFORMATION: Primer to amplify a DNA fragment derived from
      human FUT8 mRNA

<400> SEQUENCE: 18
cagcgaacac tcatcttgga a                                                21

<210> SEQ ID NO 19
<211> LENGTH: 22
<212> TYPE: DNA
<213> ORGANISM: Artificial Sequence
<220> FEATURE:
<223> OTHER INFORMATION: Primer to amplify a DNA fragment derived from
      human FUT8 mRNA

<400> SEQUENCE: 19
gccagatctg tctgtgcatg tc                                               22

<210> SEQ ID NO 20
<211> LENGTH: 20
<212> TYPE: DNA
<213> ORGANISM: Artificial Sequence
<220> FEATURE:
<223> OTHER INFORMATION: Primer to amplify a DNA fragment derived from
      human GAPDH mRNA

<400> SEQUENCE: 20
attgccctca acgaccactt                                                  20

<210> SEQ ID NO 21
<211> LENGTH: 20
<212> TYPE: DNA
<213> ORGANISM: Artificial Sequence
<220> FEATURE:
<223> OTHER INFORMATION: Primer to amplify a DNA fragment derived from
      human GAPDH mRNA

<400> SEQUENCE: 21
aggtccacca ccctgttgct                                                  20
```

COMPOSITION FOR SUPPRESSING THE EXPRESSION OF FUCOSYLTRANSFERASE

TECHNICAL FIELD

The present invention relates to a composition for suppressing expression of α1,6-fucosyltransferase (FUT8), a method of suppressing growth of a cancer cell using the composition, and a kit for the method.

BACKGROUND ART

Gene therapy for cancer has been studied for a long time, and clinical researches have actually been initiated. Furthermore, RNA-based therapeutic techniques using antisense techniques or ribozyme techniques are being developed.

Attention has been paid to RNA interference (RNAi) in *Caenorhabditis elegans*, which was reported in 1998, as a phenomenon in which gene expression is suppressed due to sequence-specific mRNA degradation caused by a double-stranded RNA (see, for example, Non-patent Document 1). It is considered that the RNA interference is caused by a mechanism in which a long double-stranded RNA is degraded by an RNase III-type activity called Dicer into a short RNA of 21 to 25 nucleotides called an siRNA (short interfering RNA), and the siRNA is then incorporated into a ribonucleic acid-protein complex called RISC (RNA-induced silencing complex), which binds to a target RNA in an ATP-dependent manner to degrade the target RNA (see, for example, Non-patent Documents 2 to 7). Thereafter, it has been reported that it is possible to suppress gene expression applying the RNA interference also in a mammalian cell (see, for example, Non-patent Documents 8 and 9). Regarding gene expression control using the RNA interference (knockdown), although there are many reports in which expression of a gene transferred from the outside is controlled, there have been few reports in which expression of an endogenous gene expressed in the steady state is knocked down.

α1,6-Fucosyltransferase (GDP-L-Fuc:N-acetyl-β-D-glucosaminide α1,6-fucosyltransferase; FUT8) is a glycosyltransferase that is involved in biosynthesis of an N-linked sugar chain of a glycoprotein, and catalyzes a reaction of attaching fucose to the 6-position of an N-acetylglucosamine residue linked to asparagine in an N-linked complex-type sugar chain. Mouse and human FUT8-encoding genes have been isolated, and the nucleotide sequences have been determined (Non-patent Documents 10 and 11). A cell in which the gene for FUT8 is knocked out for modifying sugar chain modification of an antibody has been produced (Patent Document 1). Furthermore, there is report on knockdown of a gene for FUT8 for a similar purpose (Non-patent Document 12) although the efficiency of suppressing FUT8 expression is low (56 to 65%).

α-Fetoprotein (AFP) is a glycoprotein that is produced in liver. Although it is secreted into serum at embryonic stage, it is hardly detected in serum of a healthy adult. However, the serum APF level is elevated even in an adult if the adult suffers from a hepatic disease such as hepatitis or hepatic cancer. It is known that the amount of AFP to which fucose is attached by the action of FUT8 (called AFP L3 fraction) is increased in a patient with hepatocellular carcinoma. Thus, the AFP L3 fraction is used as a marker for hepatocellular carcinoma. However, the relationship between FUT8 and hepatic cancer is not simple, the activity of FUT8 in serum of a patient with hepatic cancer is not necessarily higher than that of a healthy person, and it is considered that production of glycoproteins having attached fucose in serum, which is known to be increased in a patient with hepatic cancer, requires not only FUT8 but also cooperation with another enzyme or the like (Non-patent Document 13). To date, there has been no finding that control of FUT8 expression is effective in treating a disease.

Patent Document 1: JP-A 2005-224240
Non-patent Document 1: Nature, 391:806-811 (1998)
Non-patent Document 2: Nature, 409:363-366 (2001)
Non-patent Document 3: Genes and Development, 13:3191-3197 (1999)
Non-patent Document 4: Cell, 101:25-33 (2000)
Non-patent Document 5: Cell, 107:309-321 (2001)
Non-patent Document 6: Genes and Development, 15:188-200 (2001)
Non-patent Document 7: Cell, 107:297-307 (2001)
Non-patent Document 8: Nature, 411:494-498 (2001)
Non-patent Document 9: Proc. Natl. Acad. Sci. USA, 98:9742-9747 (2001)
Non-patent Document 10: DNA Sequence, 11:90-96 (2000)
Non-patent Document 11: J. Biochem., 121:626-632 (1997)
Non-patent Document 12: Biotechnol. Bioeng., 88:901-908 (2004)
Non-patent Document 13: Cancer Research, 63:6282-6289 (2003)

DISCLOSURE OF INVENTION

Problems to be Solved by the Invention

The main object of the present invention is to provide a means by which at least one of suppression of expression level of a gene for FUT8, suppression of expression level of an FUT8 protein, suppression of expression level of a product by the action of FUT8 and the like is attained.

Means to Solve the Problems

As a result of intensive studies, the present inventors have found an RNA capable of suppressing expression of FUT8 in a cell, and developed a nucleic acid construct from which the RNA is transcribed in a cell. Furthermore, the present inventors have found that growth of a cancer cell can be suppressed by suppressing the function of FUT8 utilizing the RNA or the nucleic acid construct. Thus, the present invention has been completed.

The present invention relates to the following.

[1] An RNA of 13 to 29 nucleotides that contains a nucleotide sequence of any one of SEQ ID NOS:1 to 4 or a portion thereof, or an RNA having a sequence complementary to said RNA, which is capable of suppressing expression of α1,6-fucosyltransferase in a cell;

[2] The RNA according to [1], which contains a nucleotide sequence of any one of SEQ ID NOS:5 to 8;

[3] The RNA according to [1] or [2], which has 2 to 4 successive deoxythymidine residues at the 3' terminus;

[4] An RNA capable of suppressing expression of α1,6-fucosyltransferase in a cell, in which the RNA defined by any one of [1] to [3] is connected to an RNA complementary to said RNA directly or via an RNA of an arbitrary sequence.

[5] A double-stranded RNA capable of suppressing expression of α1,6-fucosyltransferase in a cell, which consists of the RNA defined by any one of [1] to [3] and an RNA complementary to said RNA;

[6] A nucleic acid construct, which contains:

(1) a nucleic acid encoding an RNA of 13 to 29 nucleotides that contains a nucleotide sequence of any one of SEQ ID NOS:1 to 4 or a portion thereof placed downstream of a promoter; and (2) a nucleic acid encoding an RNA complementary to said RNA placed downstream of a promoter, wherein the nucleic acid construct is constructed so that transcription into the RNAs encoded by both of the nucleic acids can take place in a cell;

[7] The nucleic acid construct according to [6], which contains:

(1) a nucleic acid encoding an RNA containing a nucleotide sequence of any one of SEQ ID NOS:5 to 8; and (2) a nucleic acid encoding an RNA having a sequence complementary to said RNA;

[8] A nucleic acid construct, which contains a nucleic acid encoding an RNA in which an RNA of 13 to 29 nucleotides that contains a nucleotide sequence of any one of SEQ ID NOS:1 to 4 or a portion thereof is connected to an RNA complementary to said RNA directly or via an RNA of an arbitrary sequence, wherein the nucleic acid is placed downstream of a promoter, and the nucleic acid construct is constructed so that transcription into the RNA encoded by the nucleic acid can take place in a cell;

[9] The nucleic acid construct according to [8], which contains a nucleic acid encoding an RNA in which an RNA containing a nucleotide sequence of any one of SEQ ID NOS:5 to 8 is connected to an RNA complementary to said RNA directly or via an RNA of an arbitrary sequence;

[10] The nucleic acid construct according to any one of [6] to [9], which is incorporated into a vector selected from the group consisting of plasmid vectors and virus vectors;

[11] A pharmaceutical composition containing, as an active ingredient, the RNA defined by any one of [1] to [3], the double-stranded RNA defined by [4] or [5], or the nucleic acid construct defined by any one of [6] to [10];

[12] A pharmaceutical composition used for treating a cancer, which contains an RNA capable of suppressing expression of α1,6-fucosyltransferase, or a nucleic acid construct capable of expressing said RNA in a cell;

[13] The pharmaceutical composition according to [12], wherein the RNA capable of suppressing expression of α1,6-fucosyltransferase is:

(A) an RNA having a sequence complementary to a sequence of 13 to 29 successive nucleotides in the nucleotide sequence of SEQ ID NO:9;

(B) a double-stranded RNA consisting of the RNA of (A) and an RNA complementary to the RNA of (A); or (C) an RNA in which the RNA of (A) is connected to an RNA complementary to the RNA of (A) directly or via an RNA of an arbitrary sequence;

[14] The pharmaceutical composition according to [13], wherein the RNA capable of suppressing expression of α1,6-fucosyltransferase is:

(A) an RNA having a sequence complementary to a sequence of 13 to 29 nucleotides that contains a nucleotide sequence of any one of SEQ ID NOS:1 to 4 or a portion thereof;

(B) a double-stranded RNA consisting of the RNA of (A) and an RNA complementary to the RNA of (A); or (C) an RNA in which the RNA of (A) is connected to an RNA complementary to the RNA of (A) directly or via an RNA of an arbitrary sequence;

[15] The pharmaceutical composition according to [13] or [14], which contains an RNA having 2 to 4 successive deoxythymidine residues at the 3' terminus;

[16] The pharmaceutical composition according to [12], wherein the nucleic acid construct is a nucleic acid construct that contains:

(1) a nucleic acid encoding an RNA of 13 to 29 successive nucleotides in the nucleotide sequence of SEQ ID NO:9 placed downstream of a promoter; and (2) a nucleic acid encoding an RNA complementary to said RNA placed downstream of a promoter, and the nucleic acid construct is constructed so that transcription into the RNAs encoded by both of the nucleic acids can take place in a cell;

[17] The pharmaceutical composition according to [16], wherein the nucleic acid construct is a nucleic acid construct that contains:

(1) a nucleic acid encoding an RNA of 13 to 29 nucleotides that contains a nucleotide sequence of any one of SEQ ID NOS:1 to 4 or a portion thereof placed downstream of a promoter; and (2) a nucleic acid encoding an RNA complementary to said RNA placed downstream of a promoter;

[18] The pharmaceutical composition according to [12], wherein the nucleic acid construct contains a nucleic acid encoding an RNA in which an RNA of 13 to 29 successive nucleotides in the nucleotide sequence of SEQ ID NO:9 placed downstream of a promoter is connected to an RNA complementary to said RNA directly or via an RNA of an arbitrary sequence, and is constructed so that transcription into the RNA encoded by the nucleic acid can take place in a cell;

[19] The pharmaceutical composition according to [18], wherein the nucleic acid construct is a nucleic acid construct that contains a nucleic acid encoding an RNA in which an RNA of 13 to 29 nucleotides that contains a nucleotide sequence of any one of SEQ ID NOS:1 to 4 or a portion thereof placed downstream of a promoter is connected to an RNA complementary to said RNA directly or via an RNA of an arbitrary sequence.

Effects of the Invention

The present invention provides an RNA that can be used for suppressing expression of FUT8 in a cell and a nucleic acid construct that is capable of expressing the RNA in a cell. Using the RNA or the nucleic acid construct, it is possible to modify a sugar chain of a glycoprotein in a cell through suppression of FUT8 expression, or to control the generation and function of a glycoprotein. Furthermore, since it is possible to preferentially suppress growth of an FUT8-expressing cancer cell, the present invention is excellently effective in that it can be utilized for treating a cancer.

BEST MODE FOR CARRYING OUT THE INVENTION

The present invention is described in detail below.

(1) The RNA of the Present Invention

One aspect of the present invention relates to an RNA capable of suppressing expression of α1,6-fucosyltransferase (FUT8). Although the present invention is not limited to one that is based on a specific principle, the RNA can suppress the function of FUT8 by targeting an mRNA for FUT8 to degrade the mRNA or to inhibit translation of the RNA into a polypeptide.

There is no specific limitation concerning the "fucosyltransferase gene" according to the present invention as long as it encodes a polypeptide having an α1,6-fucosyltransferase activity. For example, it is exemplified by the region of exons 1 to 11 in the gene encoding human FUT8. This region encodes an mRNA of the nucleotide sequence of SEQ ID NO:9, and is preferable as a target for the RNA of the present invention (i.e., RNA capable of suppressing expression of FUT8). A region of a sequence having addition, substitution, deletion, insertion or the like of a nucleotide in SEQ ID NO:9 may also serve as a target for the RNA of the present invention. Amino acid sequences of and cDNA nucleotide sequences for FUT8 are disclosed, for example, under GenBank accession nos. D89289 (human FUT8), AB025198 (mouse FUT8) and the like.

As used herein, "capable of suppressing expression of FUT8" refers, without limitation, to being capable of suppressing expression of a gene for FUT8, or expression of an FUT8-derived cell growth signal or an FUT8 protein. In other words, the concept encompasses, for example, capability of suppressing transcription of a gene for FUT8 into an mRNA, capability of destabilizing a transcribed mRNA, capability of suppressing translation of an mRNA for FUT8 into a polypeptide, or capability of suppressing the function of a translated polypeptide.

The RNA of the present invention contains an RNA for suppressing expression of FUT8, and is an RNA molecule that is homologous or complementary to a nucleotide sequence of an mRNA encoded by a gene for FUT8, or a double-stranded RNA molecule that contains a strand of a sequence homologous to a nucleotide sequence of such an mRNA. "Homologous or complementary to a nucleotide sequence of an mRNA encoded by a gene for FUT8" not only refers to being completely homologous or complementary to a nucleotide sequence of the mRNA, but also encompasses being substantially homologous or complementary as long as the desired function is exerted. Examples of such RNA molecules include, but are not limited to, an siRNA which is a double-stranded RNA that causes RNA interference. For suppressing the interferon response in mammalian cells, the chain length of the siRNA is for example 13 to 29 nucleotides, preferably 15 to 25 base pairs, more preferably 20 to 25 base pairs. A nucleotide sequence of such length may be entirely or partially derived from a nucleotide sequence of an mRNA for FUT8. Furthermore, in view of effectiveness of RNA interference in mammalian cells, the RNA of the present invention may be in the form of a double-stranded RNA having a protruding single-stranded region of for example 2 to 4 nucleotides, preferably 2 nucleotides, on the 3'-terminal side. The protruding single-stranded region is exemplified by 2 to 4 successive deoxythimidine residues (TT, TTT, TTTT).

Although the RNA of the present invention is composed mainly of ribonucleotides, it may contain a deoxyribonucleotide, a deoxyribonucleotide derivative and/or a ribonucleotide derivative in a part thereof. Although it is not intended to limit the present invention, the RNA of the present invention can be synthesized according to a known chemical synthesis method. Alternatively, it may be prepared enzymatically (for example, using an RNA polymerase) using an appropriate template nucleic acid.

The RNA of the present invention may be modified with a chemically-modifying group or the like for stabilization or labeling. Examples of modification methods include, but are not limited to, attachment of fluorescent substance, biotinylation, 5'-phosphorylation, 2'-O-methylation, conversion into PNA (Peptide Nucleic Acid) and amination. The modification may be made at the 5' terminus, the 3' terminus or an internal nucleotide as long as the modification does not inhibit the action of suppressing expression of the gene of interest.

There is no specific limitation concerning the nucleotide sequence of the RNA molecule as long as it has a nucleotide sequence homologous or complementary to an mRNA encoded by a gene for FUT8. A method of designing the same is explained with regard to an siRNA for RNA interference as an example. In case of an siRNA, it can be designed with (I) a step of secondary structure prediction and (II) a step of siRNA sequence selection.

The secondary structure prediction in step (I) can be conducted by predicting the secondary structure of a nucleotide sequence of a gene to be suppressed using a program or the like. For efficiently causing RNA interference, it is preferable to avoid a portion that assumes a strong secondary structure. Although it is not intended to limit the present invention, the MFOLD program (http://bioweb.pasteur.fr/seqanal/interfaces/mfold-simple.html) can be used as a program for secondary structure prediction.

In step (II), an siRNA can be selected based on a nucleotide sequence of an arbitrary region of an mRNA derived from a gene to be suppressed. For example, a nucleotide sequence of a structural gene region, a 5' untranslated region, a 3' untranslated region, or a region around an initiation codon or a termination codon can be preferably used. For example, the designing can be carried out using, as a sense strand RNA, a region in such a nucleotide sequence that contains two successive adenylate residues, or two adenylate residues and one guanylate residue. Alternatively, one may select a sequence consisting of two successive adenylate residues followed by arbitrary 13 to 29 nucleotide residues, a sequence consisting of one guanylate residue and arbitrary 20 nucleotide residues, or a sequence consisting of one cytidylate residue and arbitrary 20 nucleotide residues. The present invention is not limited to the use of an RNA molecule having the above-mentioned feature. The GC content of the sense strand can be, without limitation, 30 to 70%, more preferably 40 to 60%. Preferably, for preventing nonspecific action, it is desirable to confirm, by conducting a nucleotide sequence homology search during the course of designing, that the nucleotide sequence is specific for the gene to be suppressed, that is, the sequence identity to sequences in a database of known nucleotide sequences for the cell or organism species from which the gene is derived is low.

Although it is not intended to limit the present invention, the nucleic acid of the present invention is preferably an RNA of 13 to 29 nucleotides that contains a nucleotide sequence of any one of SEQ ID NOS:1 to 4 or a portion thereof, or an RNA having a sequence complementary to said RNA, which is capable of suppressing expression of α1,6-fucosyltransferase in a cell. The nucleic acid is exemplified by an RNA that contains a nucleotide sequence of any one of SEQ ID NOS:5 to 8. The RNA may be used after attaching 2 to 4 successive deoxythymidine residues at the 3' terminus as described above. The nucleotide sequences of SEQ ID NOS:2 to 8 are sequences commonly present in mRNAs derived from mouse and human genes for FUT8.

The nucleic acid of the present invention also encompasses a double-stranded RNA consisting of the above-mentioned RNA and an RNA complementary to said RNA. Specific examples thereof include the double-stranded RNAs disclosed in Examples below as siRNA1, siRNA2, siRNA3 and siRNA4. These four double-stranded RNAs have been confirmed to be capable of suppressing transcription of a gene for FUT8 into an mRNA in a mouse cell. The nucleic acid of the present invention may be a single-stranded RNA that is capable of forming double strand intramolecularly. For example, it is exemplified by a single-stranded RNA in which an RNA of 13 to 29 nucleotides that contains a nucleotide sequence of any one of SEQ ID NOS:1 to 4 or a portion thereof is connected to an RNA complementary to said RNA directly or via an RNA of an arbitrary sequence. The single-stranded RNA having an RNA of an arbitrary sequence forms a double-stranded RNA having a stem-loop structure in which the portion of the arbitrary sequence serves as a loop. A sequence of for example 1 to 30 nucleotides, preferably 1 to 25 nucleotides, more preferably 5 to 22 nucleotides is used as the arbitrary sequence.

The suppression of FUT8 expression by the RNA of the present invention can be confirmed by measuring an enzymatic activity of FUT8, quantifying an FUT8 enzyme protein (ELISA method, Western blot method, etc.), or quantifying an amount of an mRNA for FUT8 using a gene amplification method (RT-PCR method, etc.), a nucleic acid hybridization method (Northern blot method, etc.) or the like.

(2) The Nucleic Acid Construct of the Present Invention

A nucleic acid construct capable of expressing the RNA as described above in (1) in a cell exemplifies another aspect of the composition of the present invention. This construct is useful in continuously suppressing the function of FUT8 in a cell.

Although it is not intended to limit the present invention, in the nucleic acid construct of the present invention, a nucleic acid encoding the RNA as described in (A) above is connected downstream of a promoter that is capable of exerting the function in a mammalian cell so that transcription into the RNA can take place (i.e., operably). A construct in which respective nucleic acids encoding RNA strands that constitute a double-stranded RNA capable of suppressing expression of FUT8 are placed downstream of promoters exemplifies a preferable embodiment.

There is no specific limitation concerning the promoter used for the nucleic acid construct of the present invention as long as it can function in a mammalian cell. Examples thereof include RNA polymerase II promoters, RNA polymerase III promoters and promoters that can be regulated using tetracycline. Furthermore, use of a tissue-specific promoter is advantageous in that it enables suppression of the function of FUT8 specifically in the desired cell, site, organ or the like. Examples of the RNA polymerase II promoters include, but are not limited to, CMV promoter. Examples of the RNA polymerase III promoters include tRNA promoters, U6 snRNA promoter and histone H1 promoter. Examples of the promoters that can be regulated using tetracycline include tetracycline-regulatable U6 promoter and TR promoter. Furthermore, transcription into an RNA can be controlled more strictly by using the Cre-loxP system in combination with the promoter.

A further preferable embodiment of the present invention is exemplified by a nucleic acid construct, which contains: (1) a nucleic acid encoding an RNA of 13 to 29 nucleotides that contains a nucleotide sequence of any one of SEQ ID NOS:1 to 4 or a portion thereof placed downstream of a promoter; and (2) a nucleic acid encoding an RNA complementary to said RNA placed downstream of a promoter, wherein the nucleic acid construct is constructed so that transcription into the RNAs encoded by both of the nucleic acids can take place in a cell. More specifically, it is exemplified by a nucleic acid construct which contains: (1) a nucleic acid encoding an RNA containing a nucleotide sequence of any one of SEQ ID NOS:5 to 8; and (2) a nucleic acid encoding an RNA having a sequence complementary to said nucleic acid.

Furthermore, the present invention also encompasses a nucleic acid construct, which contains a nucleic acid encoding an RNA in which an RNA of 13 to 29 nucleotides that contains a nucleotide sequence of any one of SEQ ID NOS:1 to 4 or a portion thereof is connected to an RNA complementary to said RNA directly or via an RNA of an arbitrary sequence. A single-stranded RNA that is capable of forming a stem-loop (or hairpin) structure is transcribed from the nucleic acid construct. There is no specific limitation concerning the arbitrary sequence (encoding the loop portion in the single-stranded RNA). It is exemplified by a sequence of for example 1 to 30 nucleotides, preferably 1 to 25 nucleotides, more preferably 5 to 22 nucleotides.

The nucleic acid construct may be one from which an RNA molecule corresponding to a single target region is transcribed, or one from which plural RNA molecules corresponding to plural target regions can be transcribed.

There is no specific limitation concerning the construction of the nucleic acid construct of the present invention. For example, the construction can be conducted so that transcription into sense and antisense strands of a double-stranded RNA capable of suppressing the function of the gene of interest takes place in the following system: (A) a tandem type for transcription into a sense RNA and an antisense RNA independently, in which a nucleic acid encoding the sense RNA and a nucleic acid encoding the antisense RNA are connected downstream of two different promoters, and the two transcription units are placed in the forward direction; (B) a type for transcription into an RNA of a stem-loop type (or hairpin type) in which a sense RNA and an antisense RNA are connected directly or via a loop, in which a nucleic acid encoding the sense RNA and a nucleic acid encoding the antisense RNA are placed in the forward direction downstream of a single promoter; or (C) an opposite type for transcription into both RNA strands from distinct promoters by placing the promoters at both ends of a nucleic acid encoding (on the respective strands) the sense strand and the antisense strand. According to the present invention, one can select and use the tandem type, the stem-loop type or the opposite type depending on the used conditions such as the kind of the mammalian cell, or the kinds of the sense sequence and the antisense sequence.

There is no specific limitation concerning the nucleotide sequence of the RNA capable of suppressing expression of FUT8 which is encoded by the nucleic acid construct of the present invention as long as the sequence exhibits an action of suppressing expression of FUT8 in an FUT8-specific manner. If an RNA polymerase III promoter is to be used for transcription into the RNA, it desirably fulfills with the following two requirements:

transcription initiation site being a purine residue (guanylate residue (G) or adenylate residue (A)); and two nucleotides in front of transcription initiation site being AA because of the addition of four successive uracil residues at the 3' terminus of antisense strand.

If an RNA polymerase II promoter is to be used for transcription into the RNA, the construct desirably fulfills the following requirements:

the sequence being of the stem-loop type; and a short poly(A) sequence being attached.

The nucleic acid construct of the present invention may be incorporated into an appropriate vector such as a plasmid vector or a virus vector so that it can more stably exert the effect in a cell. The nucleic acid construct of the present invention may be integrated into a chromosomal DNA in a cell.

There is no specific limitation concerning the vector used according to the present invention as long as it can maintain the nucleic acid construct of the present invention in a cell. Examples of the plasmid vectors include, but are not limited to, those for expressing a nucleic acid for RNA interference such as piGENE tRNA plasmid (product name, iGENE), siLentGene (Promega), pSEC Hygro Vector (Ambion) and pBAsi vector (Takara Bio). The virus vectors include adenovirus vectors, adeno-associated virus vectors, retrovirus vectors and lentivirus vectors. Examples of commercially available adenovirus vectors include Knockout Adenoviral RNAi System (Clontech), and examples of commercially available retrovirus vectors include pSINsi vector (Takara Bio) and pSIREN-RetroQ Vector (Clontech).

A vector into which the nucleic acid construct of the present invention is incorporated can be constructed by selecting an siRNA sequence as described above, and incorporating a promoter, a nucleic acid encoding the siRNA and optionally other elements into a vector so that transcription into the siRNA takes place. Various elements to be incorporated into a vector can be prepared using known means such as enzymatic synthesis using a PCR method or chemical synthesis.

The constructed vector can be transferred into the cell of interest according to a method suitable for the vector, for example, using an electroporation method or a lipofection method in case of a plasmid vector, or utilizing infectivity of a virus to a cell in case of a virus vector.

Suppression of FUT8 expression by the nucleic acid construct of the present invention can also confirmed using various methods as described above.

The RNA of the present invention, the nucleic acid construct of the present invention or the vector into which the construct is incorporated as described above is useful in preparation of a composition for suppressing a gene for FUT8 that contains the same as an active ingredient. The composition can be prepared by combining the active ingredient with an appropriate carrier such as a carrier that is effective in stabilizing the active ingredient or transferring the active ingredient into a cell (a buffering component, a salt, a saccharide, a protein, a surfactant, a reagent for transfection, etc.). The composition can be used as a pharmaceutical composition for treatment of a disease for which suppression of the function of FUT8 is desired. In this case, it is preferable to prepare the composition using a pharmaceutically acceptable carrier.

(3) The Pharmaceutical Composition of the Present Invention

As shown in Examples below, cell growth capacity is suppressed in a cell in which expression of FUT8 is suppressed. Thus, an RNA capable of suppressing expression of FUT8, a nucleic acid construct capable of expressing the RNA in a cell or a composition containing the same as an active ingredient disclosed herein can be used for suppressing cell growth. The pharmaceutical composition or a method of suppressing cell growth using the composition is one of the embodiments of the present invention. The pharmaceutical composition is useful in treatment, or prevention, of a disease for which suppression of cell growth is desired such as a cancer, preferably a cancer containing a cancer cell expressing FUT8 (e.g., hepatic cancer or uterine cancer) although it is not intended to limit the present invention. The dosage of the pharmaceutical composition for a patient is appropriately determined depending on the formulation, the administration route, the purpose of use as well as the age, weight and condition of the patient to which the pharmaceutical composition is to be administered.

The pharmaceutical composition of the present invention contains as an active ingredient an RNA capable of suppressing expression of FUT8 or a nucleic acid construct capable of transcribing into the RNA in a cell. Specific examples thereof include:

(A) an RNA having a sequence complementary to a sequence of 13 to 29 successive nucleotides in the nucleotide sequence of SEQ ID NO:9;

(B) a double-stranded RNA consisting of the RNA of (A) and an RNA complementary to the RNA of (A);

(C) an RNA in which the RNA of (A) is connected to an RNA complementary to the RNA of (A) directly or via an RNA of an arbitrary sequence;

(D) a nucleic acid construct that contains: (1) a nucleic acid encoding an RNA of 13 to 29 successive nucleotides in the nucleotide sequence of SEQ ID NO:9 placed downstream of a promoter; and (2) a nucleic acid encoding an RNA complementary to said RNA placed downstream of a promoter, and (E) a nucleic acid construct that contains a nucleic acid encoding an RNA in which an RNA of 13 to 29 successive nucleotides in the nucleotide sequence of SEQ ID NO:9 placed downstream of a promoter is connected to an RNA complementary to said RNA directly or via an RNA of an arbitrary sequence.

The RNA or the nucleic acid construct of the present invention as described in (1) or (2) above is particularly preferable for the pharmaceutical composition of the present invention.

If growth of a cancer cell is to be suppressed according to the present invention, a method in which a known agent is used may further be used in combination. Examples of pre-existing agents include, but are not limited to, anticancer agents such as 5FU and Taxol. Thus, the pharmaceutical composition of the present invention also encompasses a combination (as a single composition or as independent pharmaceutical compositions to be administered separately) of an anticancer agent and the pharmaceutical composition of the present invention.

A known gene transfer method can be used upon administration of the pharmaceutical composition to a patient. Although it is not intended to limit the present invention, it is possible to utilize the following, for example, for an active ingredient in a form of an RNA, a nucleic acid construct or a plasmid: an electroporation method, an intratissue injection, a hydrodynamics method, microinjection, transfection, a lipofection method, a bombardment method using gold particles, a calcium phosphate method, a DEAE-dextran method, a method using micelle particles, a method using reversed micelle particles, a method using a membrane permeable peptide, a method using a membrane-fusing peptide, a method using low-density lipoprotein, a method using transferrin, or a method using atelocollagen. If a virus vector is to be used, infection of a cell or the like may be conducted according to a method suitable for the virus vector.

The pharmaceutical composition of the present invention may assume a form of a kit containing plural components. Examples of the kits include, but are not limited to, a kit containing an RNA capable of suppressing expression of FUT8 and a reagent for transferring the RNA into a cell; a kit containing a plasmid encoding an RNA capable of suppressing expression of FUT8 and a reagent for transferring the plasmid into a cell; a kit containing a reagent for in vitro preparation of an RNA capable of suppressing expression of FUT8 (template DNA and RNA polymerase, etc.) and a reagent for transferring the RNA into a cell; and a kit containing a virus vector encoding an RNA capable of suppressing expression of FUT8 and a reagent used for infecting a cell with the virus vector. The kit brings advantageous effect in handling in particular, for example, in that it can be immediately used for administration to a patient because the active ingredient and a component for administering the same are combined therein.

It is possible to evaluate growth suppression of an FUT8-expressing cancer cell using a known method such as, without limitation, an MTT method, ELISA or immunostaining.

Furthermore, since growth of an FUT8-expressing cancer cell can be selectively suppressed according to the method of suppressing growth of a cancer cell of the present invention, the method can also be utilized as a method of treating a cancer involving a gene for FUT8. The effect of treating a cancer according to the present invention can be evaluated using a known method such as, without limitation, examination of survival benefit using an experimental animal (a cancer-carrying animal, etc.), examination of effect of suppressing tumor growth, examination by an RT-PCR method, examination by immunostaining or examination by ELISA.

As described above, FUT8 is a glycosyltransferase that is involved in biosynthesis of an N-linked sugar chain of a glycoprotein, and catalyzes a reaction of attaching fucose to the 6-position of an N-acetylglucosamine residue linked to asparagine in an N-linked complex-type sugar chain. The structure of a sugar chain on a glycoprotein having a fucose-containing N-linked complex-type sugar chain in a cell is altered by suppressing the function of FUT8 in the cell using the RNA or the nucleic acid construct of the present invention. If a fucose residue attached by FUT8 is important for the physiological activity or stability of the glycoprotein, it is possible to regulate or modify the function of the glycoprotein according to the present invention.

EXAMPLES

The following Examples illustrate the present invention in more detail, but are not to be construed to limit the scope thereof.

Example 1

Suppression of FUT8 expression by a chemically synthesized double-stranded RNA was examined using TGP49 cells (mouse pancreas cancer cells).

(1) Preparation of Double-Stranded RNA

Double-stranded RNAs having the nucleotide sequences of SEQ ID NOS:1 to 4 were prepared using for reference the nucleotide sequence of cDNA for mouse gene for FUT8 disclosed under GenBank accession number AB025198. Specifically, oligonucleotides in which two deoxythymidine residues were attached at the 3' termini of RNAs of the nucleotide sequences of SEQ ID NOS:1 to 4 were synthesized, and oligonucleotides in which two deoxythymidine residues were attached at the 3' termini of RNAs of nucleotide sequences completely complementary to SEQ ID NOS:1 to 4 were further synthesized. Oligonucleotides complementary to each other were combined to form double-stranded RNAs. Ones corresponding to SEQ ID NOS:1, 2, 3 and 4 were designated as siRNA1, siRNA2, siRNA3 and siRNA4, respectively.

(2) Transfer of RNA into Cell

TGP49 cells (mouse pancreas cancer cells; ATCC CRL-2136) were cultivated in DMEM:Ham's F12 (1:1) medium (Sigma) supplemented with 10% (by volume) fetal bovine serum (FBS), 2 mM glutamine, 50 units/ml penicillin and 50 μg/ml streptomycin in the presence of 5% (by volume) $CO_2$ at 37° C.

The thus obtained TGP49 cells were diluted with the above-mentioned medium to result in a density of $5\times10^4$ cells/ml, 1 ml of the dilution was added to each well of a 6-well plate, and the cells were cultivated to 90% confluence under the above-mentioned conditions. Each synthetic siRNA was added to the medium at a final concentration of 200 pmol and transfection was carried out. TransIT-TKO (product name, manufactured by Mirus, sold by Takara Bio) was used for transfection according to the protocol attached to the product. Transfection was carried out in a similar manner using Alexa 488-conjugated siRNA duplex (product name, Qiagen) to determine the transfection efficiency.

(3) Examination of RNA Interference Against TGP49 Cell

RNA interference of a gene for FUT8 was examined by determining change in the amount of expressed mRNA using a real-time RT-PCR method as follows.

The TGP49 cells subjected to transfection in Example 1-(2) were cultivated for 24 hours. Total RNA was extracted from the resulting cells using TRIzol™ reagent (Invitrogen), and the thus obtained extract was treated with DNase I (Takara Bio). The extraction of total RNA and the treatment with DNase I were carried out according to the manufacturers' protocols for the used reagents.

Real-time RT-PCR was conducted using 100 ng of the RNA as a template, 20 pmol each of oligonucleotides having the nucleotide sequences of SEQ ID NOS:10 and 11 as primers and SYBR Green Real-time PCR Core Kit (product name, Takara Bio). Smart Cycler II System (product name, Cepheid) was used for the reaction. The amount of mRNA derived from a gene for FUT8 in a sample was quantified under the reaction conditions of incubation at 95° C. for 10 seconds followed by 40 cycles of 95° C. for 5 seconds and 60° C. for 20 seconds. Glyceraldehyde-3-phosphate dehydrogenase (GAPDH) gene-derived mRNA was measured using primers of nucleotide sequences of SEQ ID NOS:12 and 13 in a similar manner, and the mRNA amount was standardized by calculating the relative mRNA amount (FUT8 mRNA/GAPDH mRNA).

Results of FUT8 mRNA interference by each siRNA are shown in Table 1 below. The value in Table 1 represents the percentage (%) of suppression of relative mRNA amount in a cell to which the synthetic siRNA was added, defining as 100% the relative mRNA amount in a cell subjected to transfection without the addition of the synthetic siRNA.

TABLE 1

| Cell name | siRNA1 | siRNA2 | siRNA3 | siRNA4 |
| --- | --- | --- | --- | --- |
| TGP49 | 14% | 17% | 48% | 29% |

As shown in Table 1, decrease in the amount of mRNA for FUT8 was observed using each of the siRNAs. In particular, when siRNA3 and siRNA4 were used, the amounts of mRNA for FUT8 were decreased by 48% and 29%, respectively, as compared with the case without the use of an siRNA.

When siRNA1 and siRNA2 were used, the amounts of mRNA for FUT8 were decreased by about 15% as compared with the case without the use of an siRNA. Based on the above, it was confirmed that expression of FUT8 could be efficiently suppressed using siRNA3 and siRNA4 according to the present invention.

Example 2

(1) Preparation of siRNA Expression Retrovirus

A retrovirus vector into which a unit capable of expressing an siRNA having the nucleotide sequence of SEQ ID NO:3 or SEQ ID NO:4 was incorporated was prepared in order to obtain a cell line in which the function of FUT8 was steadily suppressed.

pSINsi-mU6 DNA (product name, Takara Bio) was used as a backbone vector, and a double-stranded DNA consisting of chemically synthesized DNAs of nucleotide sequences of SEQ ID NOS:14 and 15 was incorporated between the BamHI and ClaI sites in the vector. The insertion sequence encodes an RNA of the nucleotide sequence of SEQ ID NO:3 and an RNA complementary to the sequence, and 9 nucleotides TTCAAGAGA were inserted between the RNA-encoding sequences. The plasmid constructed as described above was designated as mFUT8 siRNA #16. Similarly, a plasmid mFUT8 siRNA #5 was constructed using a double-stranded DNA consisting of DNAs of the nucleotide sequences of SEQ ID NOS:16 and 17 which encodes an RNA of the nucleotide sequence of SEQ ID NO:4 and an RNA complementary to the sequence. Retrovirus Packaging Kit Eco (product name, Takara Bio) was used for retrovirus preparation. Two plasmids contained in the kit, pGP Vector and pE-eco Vector, as well as mFUT8 siRNA #16 or mFUT8 siRNA #5 as described above were simultaneously transferred into HEK293 cells (ATCC CRL-1573). The mFUT8 siRNA #16 retrovirus or the mFUT8 siRNA #5 retrovirus was produced in a culture supernatant of a cell transformed as described above. The culture supernatant was used for gene transfer below. Similarly, a virus for mock control was prepared by simultaneously transferring pSINsi-mU6 vector without the incorporated DNA (for mock control) along with pGP Vector and pE-eco Vector into HEK293 cells.

TGP49 cells were infected with the mFUT8 siRNA #16 retrovirus or the retrovirus for mock control. Screening was carried out for a line having a transferred gene using G418 resistance as an index, and 2 lines in which FUT8 expression was steadily knocked down (KD1, KD2) and 1 mock control line (WT) were obtained.

Amounts of expressed mRNA for FUT8 in the thus obtained knocked-down lines were determined according to the method as described in Example 1-(3). The amounts of mRNA for FUT8 were suppressed by 95% for the KD1 line and 98% for the KD2 line as compared with the WT line. Furthermore, FUT8 enzymatic activities as determined according to the method of Uozumi et al. (J. Biochem., 120: 385-392 (1996)) were below the measurement limit. Thus, it was shown that expression of FUT8 was almost completely suppressed in the KD1 line and the KD2 line.

(2) Evaluation of Cell Growth Capacity of FUT8 Knocked-Down Cell Line $2 \times 10^4$ cells of KD1, KD2 or WT obtained in Example 2-(1) were placed in a well of a 96-well plate, and cultivated in DMEM:Ham's F12 (1:1) medium (Sigma) supplemented with 2% (by volume) bovine serum albumin (BSA), 2 mM glutamine, 50 units/ml penicillin and 50 μg/ml streptomycin in the presence of 5% (by volume) $CO_2$ at 37° C. Cell numbers were measured 1 to 4 days after initiation of cultivation using Cell Counting Kit-8 (product name, Wako Pure Chemical Industries). Each experiment was carried out with n=3 and the mean value was calculated.

Figure 1:
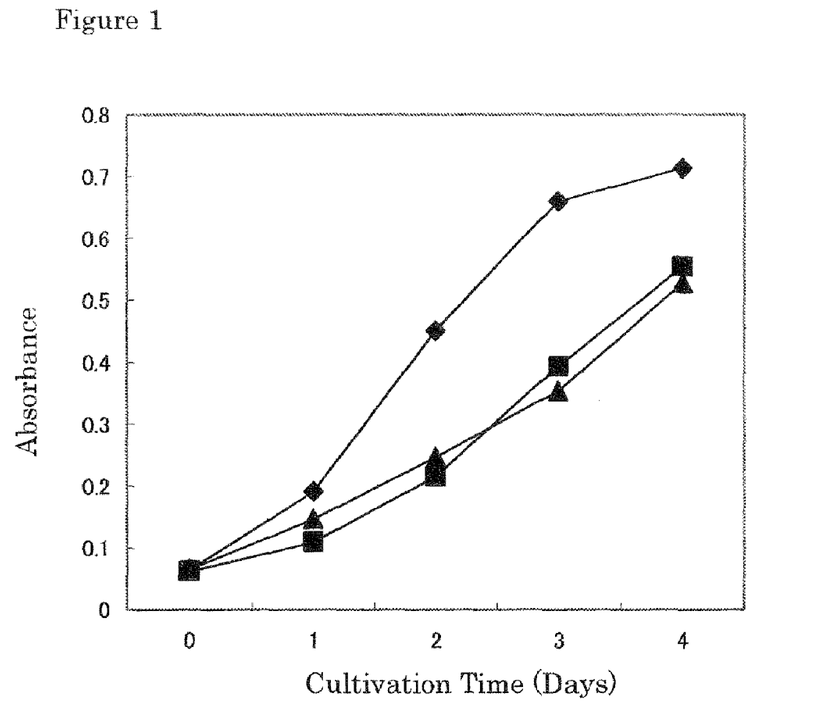
FIG. 1 illustrates growth of a cell having the nucleic acid construct of the present invention being transferred.

The time course of cell growth is shown in FIG. 1. In the figure, the longitudinal axis represents absorbance at 490 nm as an index of cell number as measured using the above-mentioned kit, and the horizontal axis represents cultivation time in days. Diamonds represent absorbance for WT, and squares and triangles represent absorbance for KD1 and KD2, respectively. As shown in FIG. 1, it can be seen that when the cell numbers were compared with that of WT, the cell growth rates for KD1 and KD2 were lower, and the final cell numbers were significantly less. Thus, the cell growth of KD1 and KD2 was suppressed as compared with WT.

Example 3

Influence of FUT8 function suppression on human hepatic cancer cells, HepG2 cells, was examined.

HepG2 cells (human hepatic cancer cells, ATCC HB-8065) were cultivated in DMEM medium (Sigma) supplemented with 10% (by volume) fetal bovine serum (FBS), 100 units/ml penicillin and 100 μg/ml streptomycin in the presence of 5% (by volume) $CO_2$ at 37° C. Retrovirus was prepared as described in Example 2-(1) except that pGP Vector and pE-ampho Vector contained in Retrovirus Packaging Kit Ampho (product name, Takara Bio) were used for transfer into HEK293 cells.

HepG2 cells were infected with mFUT8 siRNA #16-derived retrovirus. Screening was carried out for a line having a transferred gene using G418 resistance as an index, and 2 lines in which FUT8 expression was steadily knocked down were obtained. Amounts of mRNA for human FUT8 in the lines were quantified according to a real-time RT-PCR method as described in Example 1-(3) using primers of the nucleotide sequences of SEQ ID NOS:18 and 19. Primers of the nucleotide sequences of SEQ ID NOS:20 and 21 were used to measure mRNA for human GAPDH for standardizing the mRNA amount.

$2 \times 10^4$ cells of one of the knocked-down cells or HepG2 cell as the parent line were placed in a well of a 96-well plate, and cultivated in DMEM medium (Sigma) supplemented with 10% (by volume) fetal bovine serum (FBS), 100 units/ml penicillin and 100 μg/ml streptomycin in the presence of 5% (by volume) $CO_2$ at 37° C. Cell numbers were measured 1, 2, 4 or 6 days after initiation of cultivation using Cell Counting Kit-8. Each experiment was carried out with n=3 and the mean value was calculated.

Figure 2:
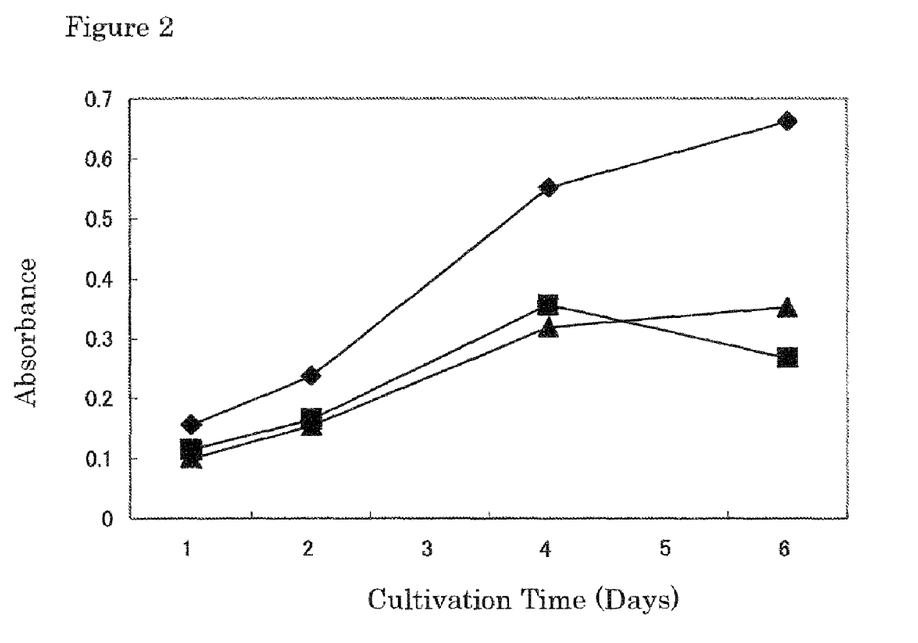
FIG. 2 illustrates growth of a cell having the nucleic acid construct of the present invention being transferred.

The time course of cell number is shown in FIG. 2. In the figure, the longitudinal axis represents absorbance at 490 nm as an index of cell number as measured using the above-mentioned kit, and the horizontal axis represents cultivation time in days. Diamonds represent absorbance for HepG2 cells, and squares and triangles represent absorbance for the respective knocked-down lines. As shown in FIG. 2, it can be seen that the cell growth rates for the knocked-down lines were remarkably lower than that of HepG2 cells, and the cell numbers attained after cultivating for 6 days were only about ½ of that of the parent strain. Thus, the cell growth of HepG2 cell in which FUT8 expression was knocked down was remarkably suppressed as compared with the parent line, HepG2 cell.

Example 4

Influence of FUT8 function suppression on human cervical cancer cells, HeLa cells, was examined.

HeLa cells (human cervical cancer cells, ATCC CCL-2) were cultivated in DMEM medium (Sigma) supplemented with 2% (by volume) FBS, 100 units/ml penicillin and 100 μg/ml streptomycin in the presence of 5% (by volume) $CO_2$ at 37° C. Retrovirus was prepared as described in Example 3 except that the plasmid mFUT8 siRNA #16, the plasmid mFUT8 siRNA #5 and pSINsi-mU6 Vector were used.

HeLa cells were infected with mFUT8 siRNA #16-, mFUT8 siRNA #5- or pSINsi-mU6 Vector (for mock control)-derived retrovirus. Screening was carried out for a line having a transferred gene using G418 resistance as an index, and 3 lines (si16-1, si16-3 and si16-4), 1 line (si5-3) and 2 lines (bG2 and bG3) were obtained as clones, respectively. Amounts of mRNA for human FUT8 in si16-3 and si5-3 were quantified according to a real-time RT-PCR method as described in Example 3, and compared with the amount of mRNA for human FUT8 in bG3 cells. As a result, decreases in amounts of mRNA for human FUT8 by 84% and 80% were observed for si16-3 and si5-3, respectively.

$2 \times 10^4$ cells of si16-4 as the knocked-down cell or bG2 as the mock control HeLa cell were placed in a well of a 96-well plate, and cultivated in DMEM medium (Sigma) supplemented with 2% (by volume) FBS, 100 units/ml penicillin and 100 μg/ml streptomycin in the presence of 5% (by volume) $CO_2$ at 37° C. Cell numbers were measured 1, 2, 3 or 4 days after initiation of cultivation using Cell Counting Kit-8. Each experiment was carried out with n=3 and the mean value was calculated.

Figure 3:
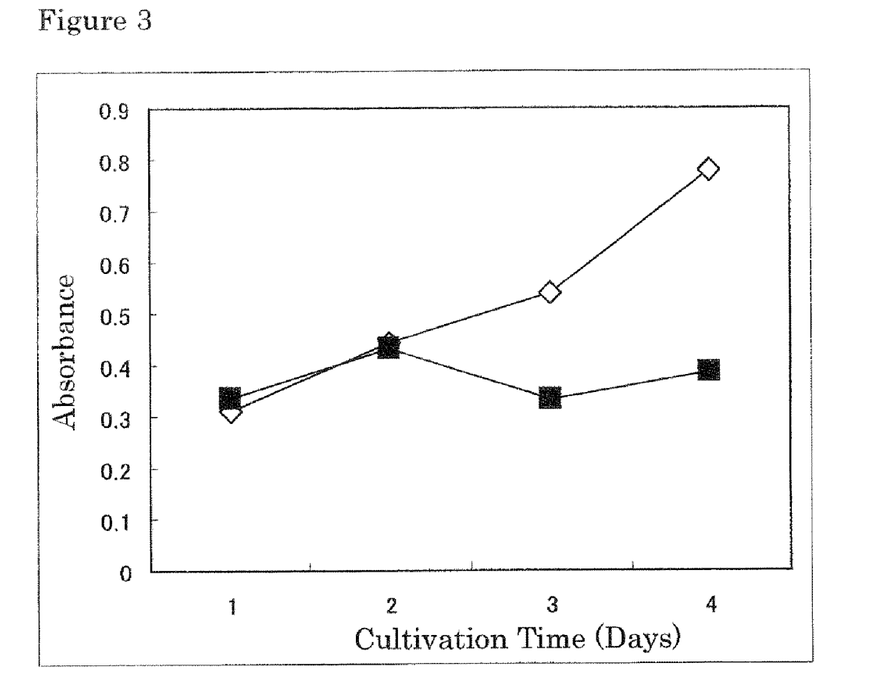
FIG. 3 illustrates growth of a cell having the nucleic acid construct of the present invention being transferred.

The time course of cell number is shown in FIG. 3. In the figure, the longitudinal axis represents absorbance at 490 nm as an index of cell number as measured using the above-mentioned kit, and the horizontal axis represents cultivation time in days. ■ and ◇ represent absorbance for si16-4 and bG2, respectively. As shown in FIG. 3, it can be seen that the cell growth rate for the knocked-down line si16-4 were remarkably lower than that of the control cell.

Figure 4:
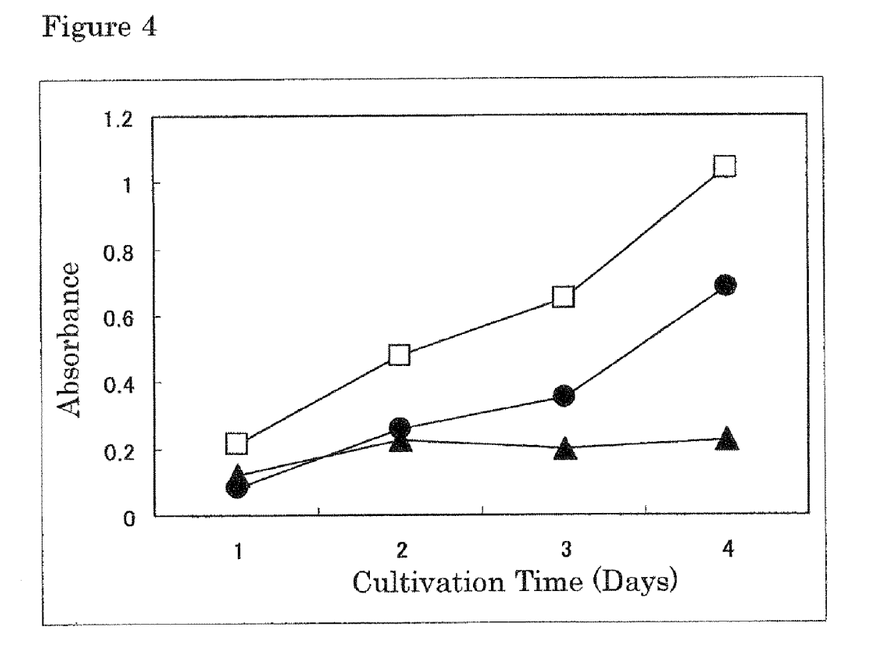
FIG. 4 illustrates growth of a cell having the nucleic acid construct of the present invention being transferred.

Furthermore, similar experiments were carried out using si16-1, si16-3 and bG3. The results are shown in FIG. 4. In the figure, ▲, ● and □ represent the time course of cell number for si16-1, si16-3 and bG3, respectively. Also in these experiments, the cell growth rates of the cell lines with the knocked-down gene for FUT8 were decreased as compared with that of the mock control cell.

As described above, the cell growth of the HeLa cell in which FUT8 expression was knocked down was remarkably suppressed as compared with the mock control cell.

INDUSTRIAL APPLICABILITY

The present invention provides an RNA capable of suppressing expression of FUT8, and a nucleic acid construct capable of transcribing into the RNA in a cell. The RNA and the nucleic acid construct are useful in selectively suppressing the function of the product of the gene in an FUT-expressing cell. Furthermore, the present invention provides a method of selectively suppressing growth of an FUT-expressing cell. The method is useful, for example, for treatment of a cancer.

Sequence Listing Free Text

SEQ ID NO:1; RNA which represses the function of FUT8 mRNA.
SEQ ID NO:2; RNA which represses the function of FUT8 mRNA.
SEQ ID NO:3; RNA which represses the function of FUT8 mRNA.
SEQ ID NO:4; RNA which represses the function of FUT8 mRNA.
SEQ ID NO:5; RNA which represses the function of FUT8 mRNA.
SEQ ID NO:6; RNA which represses the function of FUT8 mRNA.
SEQ ID NO:7; RNA which represses the function of FUT8 mRNA.
SEQ ID NO:8; RNA which represses the function of FUT8 mRNA.
SEQ ID NO:10; Primer to amplify a DNA fragment derived from mouse FUT8 mRNA.
SEQ ID NO:11; Primer to amplify a DNA fragment derived from mouse FUT8 mRNA.
SEQ ID NO:12; Primer to amplify a DNA fragment derived from mouse GAPDH mRNA.
SEQ ID NO:13; Primer to amplify a DNA fragment derived from mouse GAPDH mRNA.
SEQ ID NO:14; DNA encoding stem-loop RNA which represses the function of FUT8 mRNA.
SEQ ID NO:15; DNA encoding stem-loop RNA which represses the function of FUT8 mRNA.
SEQ ID NO:16; DNA encoding stem-loop RNA which represses the function of FUT8 mRNA.
SEQ ID NO:17; DNA encoding stem-loop RNA which represses the function of FUT8 mRNA.
SEQ ID NO:18; Primer to amplify a DNA fragment derived from human FUT8 mRNA.
SEQ ID NO:19; Primer to amplify a DNA fragment derived from human FUT8 mRNA.
SEQ ID NO:20; Primer to amplify a DNA fragment derived from human GAPDH mRNA.
SEQ ID NO:21; Primer to amplify a DNA fragment derived from human GAPDH mRNA.

The invention claimed is:

1. An RNA of at most 29 nucleotides in length, which comprises a fragment of at least 13 nucleotides within the nucleotide sequence of any one of SEQ ID NOS:1 to 4, or an RNA having a sequence complementary thereto, which is capable of suppressing expression of α1,6-fucosyltransferase in a cell.

2. The RNA according to claim 1, which contains a nucleotide sequence of any one of SEQ ID NOS:5 to 8.

3. The RNA according to claim 1, which has 2 to 4 successive deoxythymidine residues at the 3' terminus.

4. An RNA capable of suppressing expression of α1,6-fucosyltransferase in a cell, in which the RNA defined by claim 1 is connected to an RNA complementary to said RNA directly or via an RNA of an arbitrary sequence.

5. A double-stranded RNA capable of suppressing expression of α1,6-fucosyltransferase in a cell, which consists of the RNA defined by claim 1 and an RNA complementary to said RNA.

6. A nucleic acid construct, which contains:
   (1) a nucleic acid encoding an RNA of at most 29 nucleotides in length, which comprises a fragment of at least 13 nucleotides within the nucleotide sequence of any one of SEQ ID NOS:1 to 4 placed downstream of a promoter; and
   (2) a nucleic acid encoding an RNA complementary to said RNA in (1) placed downstream of a promoter,
   wherein the nucleic acid construct is constructed so that transcription into the RNAs encoded by both of the nucleic acids can take place in a cell.

7. The nucleic acid construct according to claim 6, which contains:
   (1) a nucleic acid encoding an RNA containing a nucleotide sequence of any one of SEQ ID NOS:5 to 8; and
   (2) a nucleic acid encoding an RNA having a sequence complementary to said RNA.

8. A nucleic acid construct, which contains a nucleic acid encoding an RNA in which an RNA of at most 29 nucleotides in length, which comprises a fragment of at least 13 nucleotides within the nucleotide sequence of any one of SEQ ID NOS:1 to 4, is connected to an RNA complementary to said RNA directly or via an RNA of an arbitrary sequence, wherein the nucleic acid is placed downstream of a promoter, and the nucleic acid construct is constructed so that transcription into the RNA encoded by the nucleic acid can take place in a cell.

9. The nucleic acid construct according to claim 8, which contains a nucleic acid encoding an RNA in which an RNA containing a nucleotide sequence of any one of SEQ ID NOS:5 to 8 is connected to an RNA complementary to said RNA directly or via an RNA of an arbitrary sequence.

10. The nucleic acid construct according to claim 6, which is incorporated into a vector selected from the group consisting of plasmid vectors and virus vectors.

11. A pharmaceutical composition for treating a hepatic cancer or a uterine cancer, comprising an RNA capable of suppressing expression of α1,6-fucosyltransferase, wherein the RNA capable of suppressing expression of α1,6-fucosyltransferase is:
 (A) an RNA having a sequence complementary to a sequence of at most 29 nucleotides in length, which comprises a fragment of at least 13 nucleotides within the nucleotide sequence of any one of SEQ ID NOS:1 to 4;
 (B) a double-stranded RNA consisting of the RNA of (A) and an RNA complementary to the RNA of (A); or
 (C) an RNA in which the RNA of (A) is connected to an RNA complementary to the RNA of (A) directly or via an RNA of an arbitrary sequence.

12. The pharmaceutical composition according to claim 11, which contains an RNA having 2 to 4 successive deoxythymidine residues at the 3' terminus.

13. A pharmaceutical composition for treating hepatic cancer or a uterine cancer, comprising a nucleic acid construct that contains:
 (1) a nucleic acid encoding an RNA of at most 29 nucleotides in length, which comprises a fragment of at least 13 nucleotides within the nucleotide sequence of any one of SEQ ID NOS:1 to 4 placed downstream of a promoter; and
 (2) a nucleic acid encoding an RNA complementary to said RNA placed downstream of a promoter.

14. A pharmaceutical composition for treating hepatic cancer or uterine cancer, comprising a nucleic acid construct that contains a nucleic acid encoding an RNA in which an RNA of at most 29 nucleotides in length, which comprises a fragment of at least 13 nucleotides within the nucleotide sequence of any one of SEQ ID NOS:1 to 4 placed downstream of a promoter, is connected to an RNA complementary to said RNA directly or via an RNA of an arbitrary sequence.

15. The nucleic acid construct according to claim 8, which is incorporated into a vector selected from the group consisting of plasmid vectors and virus vectors.

* * * * *